US00PP16362P3

(12) United States Plant Patent
Allen

(10) Patent No.: US PP16,362 P3
(45) Date of Patent: Mar. 21, 2006

(54) ***BETULA* PLANT NAMED 'SHILOH SPLASH'**

(50) Latin Name: *Betula nigra*
Varietal Denomination: Shiloh Splash

(76) Inventor: John D. Allen, 164 Allen Rd., Harmony, NC (US) 28634

( * ) Notice: Subject to any disclaimer, the term of this patent is extended or adjusted under 35 U.S.C. 154(b) by 66 days.

(21) Appl. No.: 10/915,564

(22) Filed: Aug. 10, 2004

(65) Prior Publication Data

US 2006/0037118 P1 Feb. 16, 2006

(51) Int. Cl.
*A01H 5/00* (2006.01)

(52) U.S. Cl. ..... Plt./216

(58) Field of Classification Search ..... Plt./226, Plt./216

See application file for complete search history.

*Primary Examiner*—Anne Marie Grunberg
*Assistant Examiner*—June Hwu
(74) *Attorney, Agent, or Firm*—Myers Bigel Sibley & Sajovec, P.A.

(57) ABSTRACT

'Shiloh Splash' is a distinctive variety of *Betula nigra*, which is characterized by its combination of distinct variegated foliage and slow growth rate as compared with other cultivars of *Betula nigra*.

2 Drawing Sheets

Latin name of the genus and species: The Latin name of the novel variety disclosed herein is *Betula nigra* L. 'Shiloh Splash'.

Variety denomination: The inventive variety of *Betula nigra* disclosed herein has been given the variety denomination 'Shiloh Splash'.

BACKGROUND OF THE INVENTION

The present invention relates to a new and distinct cultivar of *Betula nigra* grown for use as a large ornamental shrub or medium-sized tree. In general, *Betula nigra* cultivars are commonly known as river birch and are used for their showy bark which develops a creamy orange color and exfoliates in large thin sheets.

Parentage: 'Shiloh Splash' was discovered in 1999 as a branch mutation (sport) growing on a seedling river birch tree of unknown parentage in a cultivated area at Shiloh Nursery, Harmony, N.C.

Asexual reproduction. 'Shiloh Splash' was first asexually propagated by grafting at North Carolina State University, Fletcher, N.C. in February 2001. The characteristics of the new cultivar have remained stable and true to type through successive asexual propagations of grafting and stem cuttings.

SUMMARY OF THE INVENTION

'Shiloh Splash' is a distinctive variety of *Betula nigra*, which is characterized by its combination of unique variegated foliage and slow growth rate as compared with other *Betula nigra* cultivars.

Figure 1:
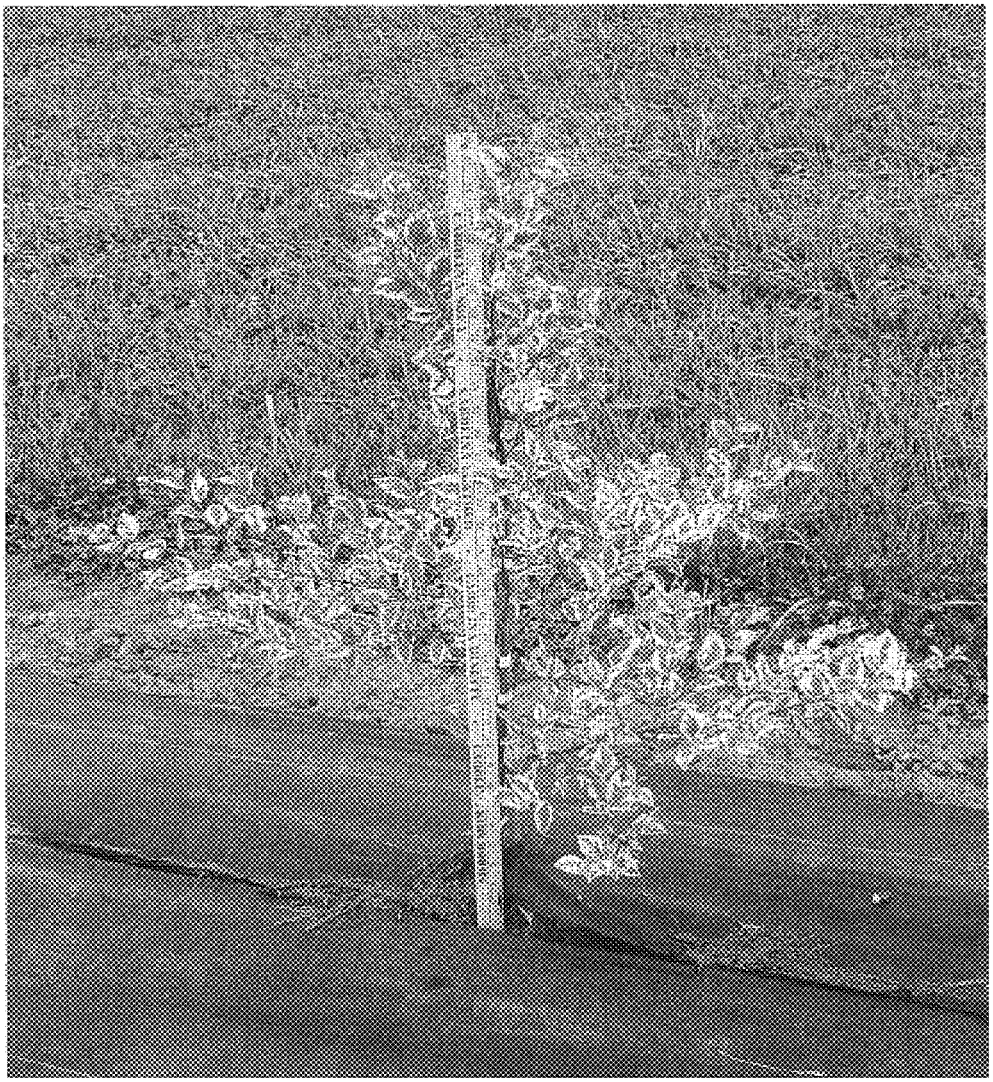
FIG. 1 illustrates the unique variegated foliage and form of a two-year old field-grown 'Shiloh Splash' plant that was originally propagated as a 15-cm stem cutting.

The photographs in the drawings were made using conventional techniques and show the colors as true as reasonably possible by conventional photography. Colors in the photographs may differ slightly from the color values cited in the detailed botanical description, which accurately describe the colors of the new *Betula nigra* 'Shiloh Splash'.

DETAILED BOTANICAL DESCRIPTION OF THE VARIETY

The following is a detailed botanical description of a new and distinct variety of *Betula nigra* known as 'Shiloh Splash' based upon observations of 3-year old plants grown in Fletcher, N.C.

Those skilled in the art will appreciate that certain characteristics will vary with older or, conversely, with younger plants. 'Shiloh Splash' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2001 edition.

'Shiloh Splash' is a large shrub or medium-sized deciduous tree of *Betula nigra* useful for landscaping. 'Shiloh Splash' has uniquely variegated foliage and a slow growth rate. These characteristics are unusual for *Betula nigra* as these plants are generally large, rapidly growing trees with medium to dark green leaves. A botanical description of 'Shiloh Splash' and comparisons with other varieties of *Betula nigra* are provided below.

Technical Description of the Variety.

Classification: Tree.

Type: Deciduous.

Commercial classification: 'Shiloh Splash' serves as a large shrub to medium-sized tree.

Use: Landscape.

Plant size: After 3 growing seasons, the plant has a height of approximately 112 cm and a width of approximately 60 cm.

Vigor: Growth rate is about 25 to 50 cm per year, which is approximately one-quarter to one-half the growth rate of typical river birch.

Trunk: Trunk diameter is approximately 1.5 to 2.5 cm at 5 cm from base. 'Shiloh Splash' can be grown with single or multiple trunks.

Bark: Trunk bark is initially smooth, and then becomes progressively more coarse with increasing trunk diameter. Bark begins to exfoliate on approximately 1 to 2 cm diameter branches with papery exfoliating sheets on larger branches and stem.

The bark color of young branches (less than 1 cm in diameter) is brownish-red (ranging between and including RHS 165A, RHS 165B, and RHS 177A). The outside color of larger branches and the trunk varies from grayish-white (ranging between and including RHS 155D, RHS 156D and RHS 156C) to grey-orange (ranging between and including RHS 164C and RHS 164D) while the inside color is golden brown (ranging between and including RHS 165A and RHS 165C).

Armature: None.

Shoots: Shoots are irregularly shaped with an alternate arrangement. In one growing season, lateral shoots typically attain a diameter of approximately 2 to 5 mm at the point of attachment to the trunk. Shoots are initially green (RHS 143C) and become grey-brown (RHS 199B) as the plant matures. Shoot surface is initially pubescent and becomes glabrous. Angle of attachment ranges from about 45 to 60 degrees.

Lenticels: Lenticels are numerous (approximately 18–25 per square cm on 0.5 cm diameter shoots and 15–20 per square cm on 2 cm diameter shoots). Color is ivory (ranging between and including RHS 164D and RHS 159C). Size varies from about 0.5 to 2 mm in length.

Leaves: Simple, ranging in length from about 3 to 11 cm and ranging in width from about 1.5 to 9 cm depending on the environment and time of year. Leaves are alternately arranged. Shape—rhombic to ovate; apex—acute; base—acute to truncate; and division—simple.

Venation: Pinnate. Number—approximately 7 to 11 pairs; margins—doubly serrate.

Foliage color: Typically variegated as described below.

Young leaves, upper side (adaxial): Margins are light green-yellow (ranging between and including RHS 1C to RHS 1D and RHS 150D) to yellow (ranging between and including RHS 2C to RHS 2D, RHS 3C to RHS 3D, and RHS 6D) with occasional highlights and/or blushing of orange-red (ranging between and including RHS 34B to RHS 34C and RHS N34C). Center of leaves are green (ranging between and including RHS 141B, RHS 143A, and RHS 139B to RHS 139C).

Young leaves, lower side (abaxial): Margins are light yellow (ranging between and including RHS 3C to RHS 3D, RHS 4D, and RHS 6D). Center of leaves are light green (RHS N138C) to grey-green (RHS 189B).

Mature leaves, upper side (adaxial): Typically have a range of color shades starting with lightest of the margin, including white (RHS 155D) to yellow (RHS 2D) with different shades of green (ranging between and including RHS N138C to RHS 139C, RHS 138A-B, and RHS 139A) moving toward the midrib of the leaf. Occasionally some leaves are completely green (ranging between and including RHS N138C to RHS 139C, RHS 138A-B, and RHS 139A) or completely yellow (ranging between and including RHS 2D to RHS 155A to RHS 155D). Occasionally some leaves only express variegation on one side of the leaf.

Mature leaves, lower side (adaxial): Margins are white (RHS 155D) to yellow (ranging between and including RHS 4D and RHS 11D). Center of the leaves are grey-green (ranging between and including RHS 188B to RHS 188D and RHS 191B to RHS 191D).

Leaf texture: Texture of the leaves is glabrous on the adaxial surface and glaucous on the abaxial surface.

Leaf attachment: Petiolate. The petiole is slightly pubescent. Length approximately 0.5 to 1.5 cm; diameter—approximately 1 to 2 mm at base; color—greyed-orange (ranging between and including RHS 166A and RHS 166C).

Buds: Imbricate. Length—about 0.4 to 0.6 cm; color—greyed-orange (RHS 165A).

Flowers/reproductive organs: No flowers observed to date.

Seed: No seed observed to date.

Pest Resistance: No significant diseases or pests observed for plants growing in Fletcher, N.C.

Cultural conditions: 'Shiloh Splash' tolerates full sun or partial shade and is best adapted to moist fertile soil with a pH of 6.0 or lower. It is contemplated that 'Shiloh Splash' is hardy in USDA Zones 4 to 9.

Propagation: 'Shiloh Splash' has been propagated by stem cuttings or grafting.

Figure 2:
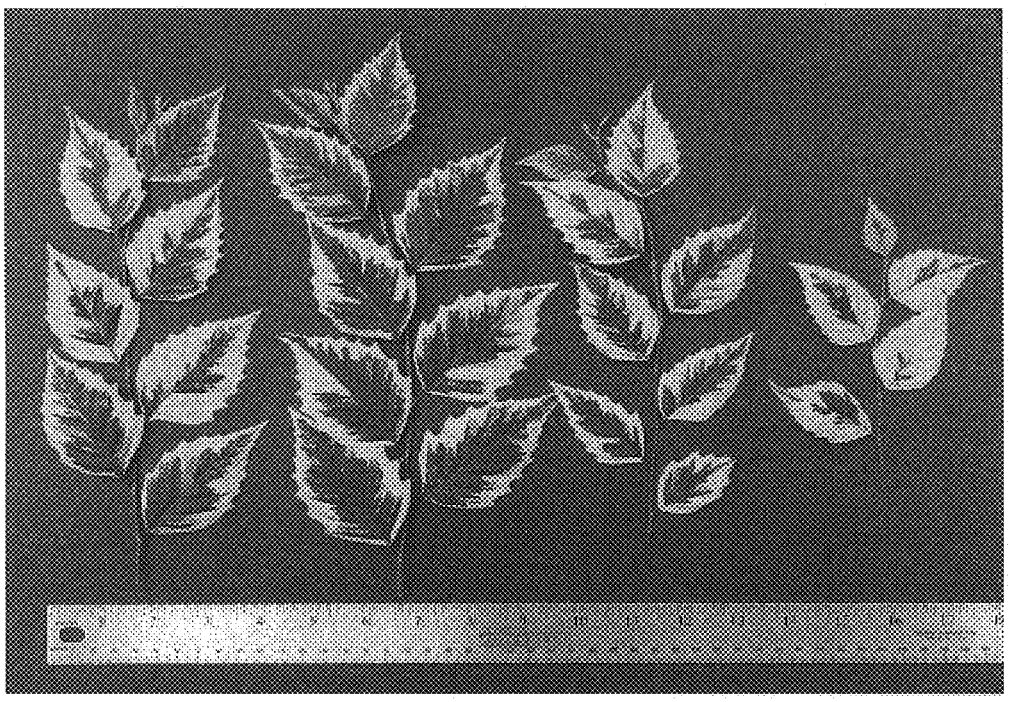
FIG. 2 shows typically variegated shoots from greenhouse-grown 'Shiloh Splash' plants.
Figure 3:
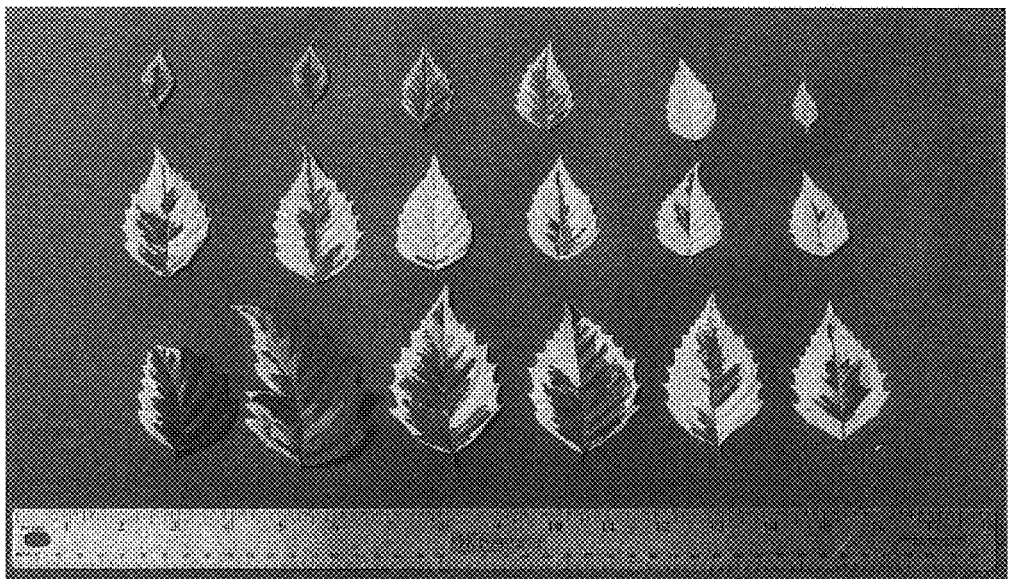
FIG. 3 illustrates the typical range of colors and patterns of leaves of 'Shiloh Splash' plants.

These and other features and characteristics of 'Shiloh Splash' are apparent from FIGS. 1–3.

Comparisons with other *Betula nigra*.

'Shiloh Splash' is distinguishable from other known cultivars of *Betula nigra*, including 'BNMTF' (unpatented; sold under the name Dura-Heat®), 'Little King' (unpatented), 'Graceful Arms' (unpatented), 'Cully' (unpatented; sold under the name Heritage®), 'Suwanee' (unpatented), 'Studetec' (unpatented; sold under the name Tecumseh Compact®) and 'Summer Cascade' (U.S. Plant Pat. No. 15,105) by its distinct variegated foliage. Further, the growth rate of 'Shiloh Splash' is slower than the growth rate of 'BNMTF', 'Graceful Arms', 'Cully', 'Suwanee', and 'Summer Cascade' and similar to that of 'Little King' and 'Studetec'.

That which is claimed is:

1. A new and distinct variety of *Betula nigra* plant named 'Shiloh Splash', substantially as described and illustrated herein.

* * * * *